United States Patent
Andersen et al.

(10) Patent No.: US 8,647,316 B2
(45) Date of Patent: *Feb. 11, 2014

(54) FOLDABLE OSTOMY BAG FOR REDUCING COLLECTING VOLUME

(75) Inventors: Birthe Vestbo Andersen, Espergaerde (DK); Soeren Hansen, Helsingoer (DK); Eskil Hoejland Olsen, Humlebaek (DK)

(73) Assignee: Coloplast A/S, Humlebaek (DK)

( * ) Notice: Subject to any disclaimer, the term of this patent is extended or adjusted under 35 U.S.C. 154(b) by 160 days.

This patent is subject to a terminal disclaimer.

(21) Appl. No.: 13/177,562

(22) Filed: Jul. 7, 2011

(65) Prior Publication Data

US 2011/0319843 A1 Dec. 29, 2011

Related U.S. Application Data

(63) Continuation of application No. 10/480,471, filed as application No. PCT/DK02/00400 on Jun. 13, 2002, now Pat. No. 8,002,759.

(30) Foreign Application Priority Data

Jun. 15, 2001 (DK) .......................... PA 2001 00935
Jun. 13, 2002 (DK) ....................... PCT/DK02/00400

(51) Int. Cl.
*A61M 5/44* (2006.01)

(52) U.S. Cl.
USPC ............................ 604/332; 604/317; 604/326

(58) Field of Classification Search
USPC .................................. 604/317, 327, 332–345
See application file for complete search history.

(56) References Cited

U.S. PATENT DOCUMENTS

| | | | | |
|---|---|---|---|---|
| 2,520,831 | A * | 8/1950 | Chincholl | 604/335 |
| 4,233,977 | A * | 11/1980 | Mattson | 604/335 |
| 4,330,060 | A * | 5/1982 | Thornton | 206/459.5 |
| 4,331,148 | A * | 5/1982 | Steer et al. | 604/333 |
| 5,248,308 | A * | 9/1993 | von Emster | 604/337 |
| 6,336,918 | B1 * | 1/2002 | Olsen et al. | 604/332 |
| 6,419,664 | B1 * | 7/2002 | von Bulow et al. | 604/337 |
| 6,516,469 | B1 * | 2/2003 | Schaetzel | 2/16 |
| 6,858,023 | B2 * | 2/2005 | Poulsen | 604/335 |
| 8,002,759 | B2 * | 8/2011 | Andersen et al. | 604/343 |
| 2003/0073962 | A1 * | 4/2003 | Olsen et al. | 604/327 |
| 2004/0030314 | A1 * | 2/2004 | LaVon et al. | 604/380 |
| 2005/0159717 | A1 * | 7/2005 | Holtermann | 604/332 |

FOREIGN PATENT DOCUMENTS

WO WO 99/66859 * 12/1999

* cited by examiner

*Primary Examiner* — Michele M Kidwell
(74) *Attorney, Agent, or Firm* — Coloplast Corp., Coloplast A/S; Nick Baumann

(57) ABSTRACT

An ostomy receiving bag includes front and rear walls sealed along a rim of the bag and a cover sheet attached to the bag. The bag has a lateral midline located between an upper end of the bag and a bottom end of the bag, with an inlet opening nearer to the upper end than to the bottom end of the bag. The cover sheet is attached to the upper end of the bag at the rim and covers at least part of one of the walls to form a pocket and an unattached edge between the upper end of the bag and the bottom end of the bag. A collecting volume of the bag is reduced by at least 25% when the bottom end of the bag is placed under the cover sheet to a position between the lateral midline and the upper end of the bag.

18 Claims, 4 Drawing Sheets

FOLDABLE OSTOMY BAG FOR REDUCING COLLECTING VOLUME

BACKGROUND OF THE INVENTION

1. Field of the Invention

The present invention relates to a collecting bag to be secured to the abdomen of a patient or to a body side ostomy member for collecting fluids or excretions emerging from an abdominal stoma.

In connection with surgery for a number of diseases in the gastro-intestinal or 10 urinary tract a consequence is, in many cases, that the colon, the ileum or the ureter has been exposed surgically and the patient is left with an abdominal stoma, or, in nephrostomy or ureterostomy, the ureter or a catheter is exposed in the back or the chest region or abdominal region, and the effluents or waste products of the body, which are conveyed through these organs, are discharged through the artificial orifice or opening and are collected in a collection bag, which is usually adhered to the skin by means of an adhesive wafer or plate having an inlet opening for accommodating the stoma/ureter/catheter. Also in connection with a fistula, the patient will have to rely on an appliance to collect the bodily material emerging from such opening.

Ostomy appliances are well known. Such appliances may be two-piece or one-piece appliances. In both types of appliances, an adhesive barrier member (or base plate) is attached to the wearer's abdomen/back/chest. In case of a one-piece appliance, a receiving member or bag is attached to the base plate. In case of a two-piece appliance, the adhesive barrier member forms part of a body side member and a receiving member or bag is attached releasably to the body side ostomy member for receiving exudates from the stoma.

When using one-piece appliances, the whole appliance, including the adhesive skin barrier securing the appliance to the skin is normally removed and replaced by a fresh appliance. When using two-piece appliances, the body side ostomy member is left in place up to several days, and only the receiving member or bag attached to the body side member is replaced. The attachment means for attaching an ostomy receiving bag may be a system known per se comprising matching coupling rings or matching flanges and adhesive surfaces engaging with and sealing against a flange area of the body side member.

Ostomy receiving bags are available in various sizes for taking into account the different need for collecting capacity of the users, both the difference between different users and also for the individual user according to actual situation and diet. The different sizes may also allow the user to use a small bag or cap for discretion when e.g. when going out or attending public meetings.

However, as the secretion of exudates from the stoma cannot be regulated at will, situations often occur where the actual size of a more discreet collecting bag is not sufficient which may cause severe embarrassment for the user.

Thus, there is a need for a very discreet collecting bag which also offers a solution to an acute demand for a larger capacity of the collecting device.

2. Description of the Related Art

GB 2 247 172 discloses a disposable ostomy receiving bag comprising front and rear walls sealed together along the rim thereof and having a top end and a bottom end wherein the top end of the rear wall is provided with an inlet opening, wherein the rear wall of the receiving bag is provided with a further cover of a sheet material which cover layer terminates at a lower edge thereof.

GB 2 094 153 discloses a disposable ostomy receiving bag comprising front and rear walls sealed together along the rim thereof and having a top end and a bottom end wherein the top end of the rear wall is provided with an inlet opening, wherein the rear wall of the receiving bag is provided with a further cover of a sheet material, which cover layer is secured to the lower part of the wall.

None of the references disclose nor indicate a solution to the problem of having an ostomy receiving bag which may be small and discrete and which at the same time also offers the option of providing a larger capacity if needed.

SUMMARY OF THE INVENTION

The present invention relates to a disposable ostomy receiving bag comprising front and rear walls sealed together along the rim thereof and having a top end and a bottom end wherein the top end of the rear wall is provided with an inlet opening, wherein the receiving bag is provided with a further cover of a sheet material covering one or both surfaces thereof.

BRIEF DESCRIPTION OF THE DRAWINGS

The invention is disclosed more in detail with reference to the drawings in which.

DETAILED DESCRIPTION OF THE PRESENT INVENTION

Figure 1:
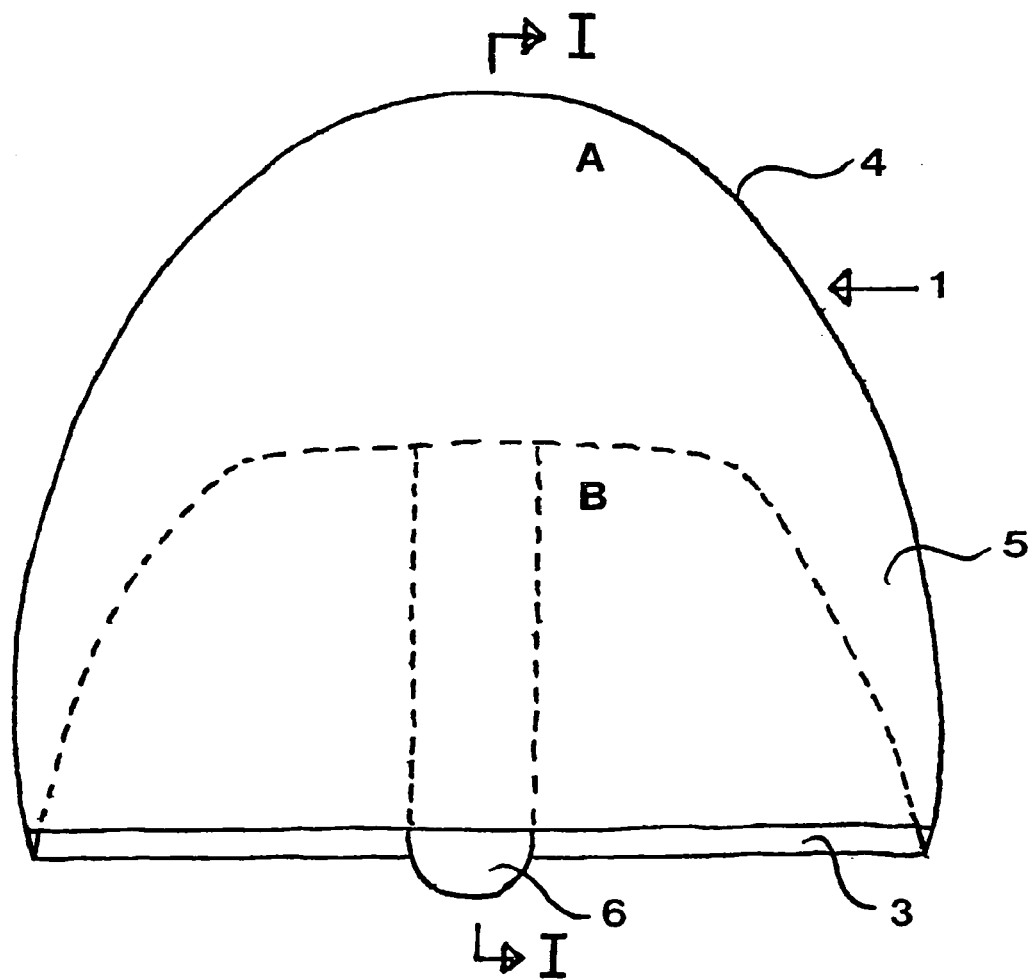
FIG. 1 shows an embodiment of an ostomy receiving bag according to the Invention.

The present invention relates to a disposable ostomy receiving bag comprising front and rear walls sealed together along the rim thereof and having a top end and a bottom end wherein the top end of the rear wall is provided with an inlet opening, wherein the receiving bag is provided with a further cover of a sheet material covering at least one of the surfaces thereof, wherein the cover sheet is provided with a cut defining a part of the cover which only covers a part of the corresponding wall and is only secured to the wall along the part of the rim being superimposed on the sealed rim of the front and rear walls, said receiving bag being characterised in that the bottom end of the bag is folded back and stretches under the cover sheet.

Thus, the present invention relates to a collecting bag to be secured to the abdomen of a patient or to a body side ostomy member for collecting fluids or excretions.

One embodiment of the invention, in which the cut cover sheet only covers the corresponding surface partly, offers an option of folding the bag and putting the folded part under the cover sheet This folding reduces the size of the bag and keeps the folded end discreetly hidden under the cover sheet and thus ensures discretion. Furthermore, it allows for an easy enlargement of the active volume of the bag simply by withdrawing the end of the bag from under the cover sheet, should a larger collecting volume suddenly be needed in situations where there is difficult or no access to a rest room.

When the cover sheet of the front wall is cut along a line perpendicular to the longest dimension of the front wall the end of the bag is easy to insert and withdraw from behind the cover sheet.

In a preferred embodiment the cover sheet covers the front wall.

It is preferred that the cover sheet of the front wall superimposing the top end of the front wall forms a pocket which will not give rise to folding of the top part of the cover sheet.

It has been found suitable when the length of the cover sheet of the front wall is from 25 to 100% of the longest dimension of the front wall which still allows for a considerable temporary reduction of the volume of the bag and reduces the use of raw materials. Thus, it is foreseen that the cover sheet may be in the form of a band covering a part of the front wall.

It is preferred that the cut of the cover sheet of the front wall is placed at a length of from 50 to 75% of the longest dimension of the front wall.

In an another embodiment of the invention, the cover sheet being cut covers all of the surface of the corresponding wall and is secured to the wall along the part of the rim being superimposed on the sealed rim of the front and rear walls leaving a slit defining two pockets each covering an end part of the bag.

In a further preferred embodiment of the invention the end of the bag opposite the top end is provided with a strip of material extending from the bottom end which will render it easier to grasp and withdraw the folded end of the bag from behind the cover sheet.

It is especially preferred that the length of the strip is longer than the distance from the bottom end of the bag in its folded state to the cut off line of the cover sheet as the end of the strip will then protrude from behind the cover sheet and thus be easier to grasp.

Furthermore, it is preferred to secure the strip in a manner that allows an easy removal, so that it e.g. can be torn off, naturally without risk of damaging the welding of the pouch which might lead to leaks, after the expansion or unfolding of the bag in order to reduce any discomfort by the strip stretching from below the pouch in the unfolded state. Thus, it is preferred that the ultimate strength of the strip in the area in which it is secured to the pouch is lower than the tearing strength of the welding of the rim of the pouch.

This may be achieved by securing the strip to the rim of the bag using a welding being weaker than the welding of the rim of the pouch and also weaker than the ultimate strength of the strip itself. Alternatively, the strip may be provided with one or more notches or perforations near the area, in which it is secured to the pouch in order to ensure that the ultimate strength in this area is lower than the tearing strength of the welding of the rim of the pouch. The strip may be of any suitable material being compatible with the cover sheet and fulfilling the above requirements.

It is preferred that the cover sheet is of a porous material as such material may reduce noise from the bag and improve the "breathing" of the skin covered by the bag.

The ostomy receiving bag according to the invention may be adapted for use together with an ostomy body side member (2-piece appliance) wherein the receiving bag is provided with coupling means for releasable securing to matching coupling means placed on the ostomy body side member and wherein the inlet opening is adapted for alignment with a hole of the ostomy body side member for receiving a stoma.

The ostomy receiving bag according to the invention may, as an alternative, be adapted for use directly (1-piece appliance) in which case the bag is provided with an adhesive wafer for securing the receiving bag to the user's skin, said bag and wafer having an inlet opening for receiving a stoma.

The receiving bag itself comprising front and rear walls sealed together along the rim and provided with an inlet opening may be made in analogy with and from materials conventionally used for the preparation of ostomy appliances. An ostomy body side member for use together with an ostomy receiving bag according to the invention may be produced from standard materials normally used for preparation of disposable ostomy and wound and incontinence devices.

Thus, the adhesive wafer for a body side member or of a 1-piece ostomy appliance bag according to the invention may be made from a medical grade barrier adhesives known in the such as the formulation being disclosed, for example in U.S. Pat. Nos. 4,367,732, 5,051,259 or 5,714,225. For a 2-piece ostomy appliance according to the invention the body side member and the receiving bag are provided with matching coupling means.

The coupling means for use in connection with the present invention may be any suitable coupling means known per se for coupling of ostomy base plates to ostomy collecting bags, e.g. a mechanical coupling such as matching coupling rings such as the coupling rings disclosed in WO 93/18725 or WO 94/18919 or matching flanges for adhesive connection of the type disclosed in U.S. Pat. No. 5,800,415.

Suitable porous materials for use as cover for the purpose of the present invention are woven or non-woven sheet materials which are moisture resistant and may be united with materials conventionally used in the production of ostomy appliances such as non-woven materials of polyethylene, polypropylene or a polyester.

DESCRIPTION OF THE PREFERRED EMBODIMENTS

The invention is now explained more in detail with reference to the drawings showing preferred embodiments of the invention.

In FIG. 1 of the drawings is shown an embodiment of a disposable ostomy receiving bag (1) according to the invention comprising front and rear walls (3) sealed together along the rim (4) thereof and having a top end (A) and a bottom end wherein the top end of the rear wall is provided with an inlet opening (not shown), wherein the receiving bag is provided with a further cover of a sheet (5) material covering one or both surfaces thereof wherein the cover sheet at at least one of the surfaces only covers a part of the corresponding wall and is only secured to the wall along the part of the rim (4) being superimposed on the sealed rim of the front and rear walls. The bottom end (B) is folded back and stretches under the cover sheet (5) of the front wall as indicated thorough a dotted line and is provided with a strip (6) of a sheet material extending from the bottom end.

Figure 2:
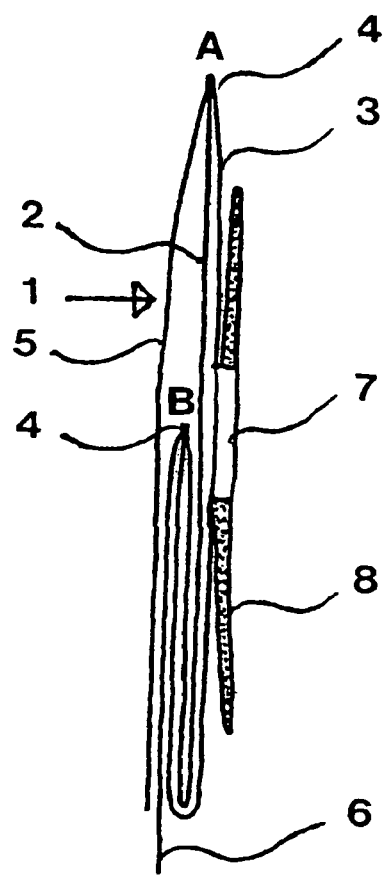
FIG. 2 shows a sectional view along the line I-I of the embodiment of FIG. 1.

FIG. 2 shows a sectional view along the line I-I of the embodiment of FIG. 1, showing the front (2) and rear (3) walls sealed together along the rim (4) thereof and having a top end (A) and a bottom (B) end. The top end of the rear wall is provided with an inlet opening (7), wherein the receiving bag is provided with a further cover (5) of a sheet material covering one or both surfaces thereof wherein the cover sheet at at least one of the surfaces only covers a part of the corresponding wall and is only secured to the wall along the part of the rim (4) being superimposed on the sealed rim of the front and rear walls. The bottom end (B) is folded back and stretches under the cover sheet (5) of the front wall and is provided with a strip (6) of a sheet material extending from the bottom end. Furthermore, the ostomy receiving bag (1) is provided with an adhesive wafer (8) for securing the same to the skin of an ostomate or to a body side member.

Figure 3:
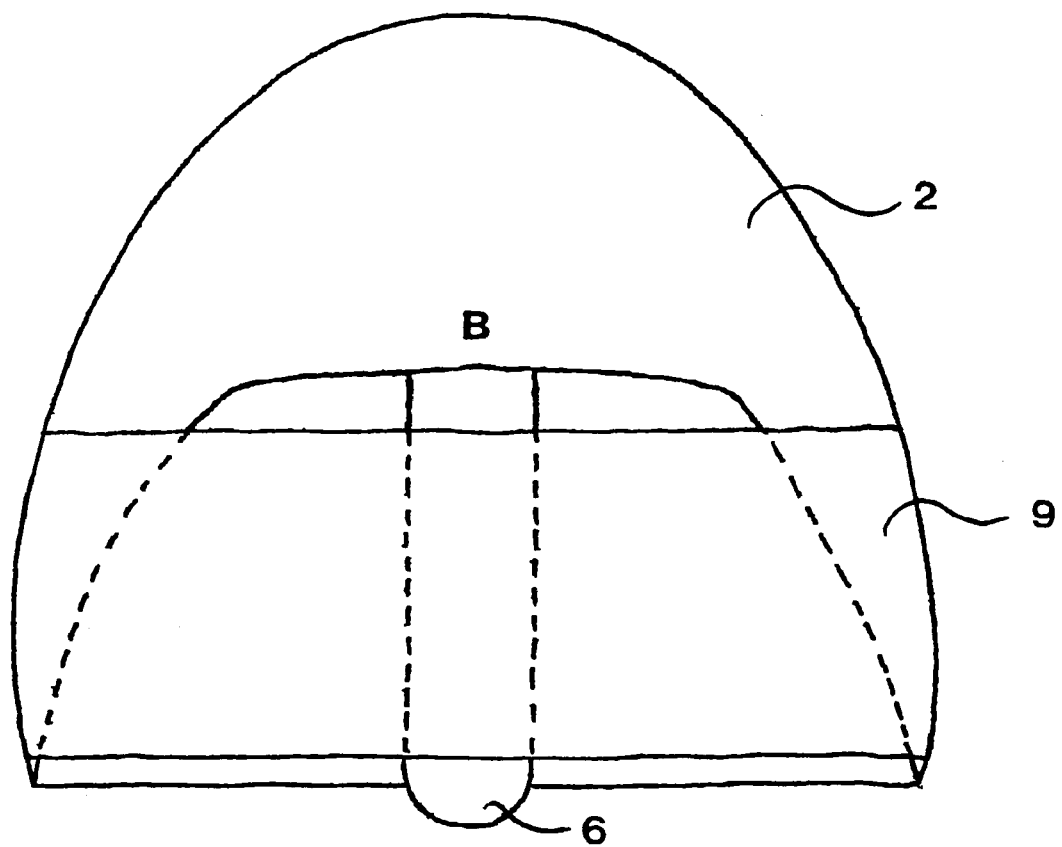
FIG. 3 shows a further embodiment of an ostomy receiving bag according to the invention.

FIG. 3 shows a further embodiment of an ostomy receiving bag according to the invention wherein the cover sheet of the front wall (2) is cut off at a length of from 25 to 80% of the longest dimension of the front wall and is in the form of a band (9) covering a part of the front wall. The bottom end B) is folded back and stretches under the cover sheet (9) of the front wall (2) and the ends of the strip (6) of a sheet material are visible above and below the cover sheet.

Figure 4:
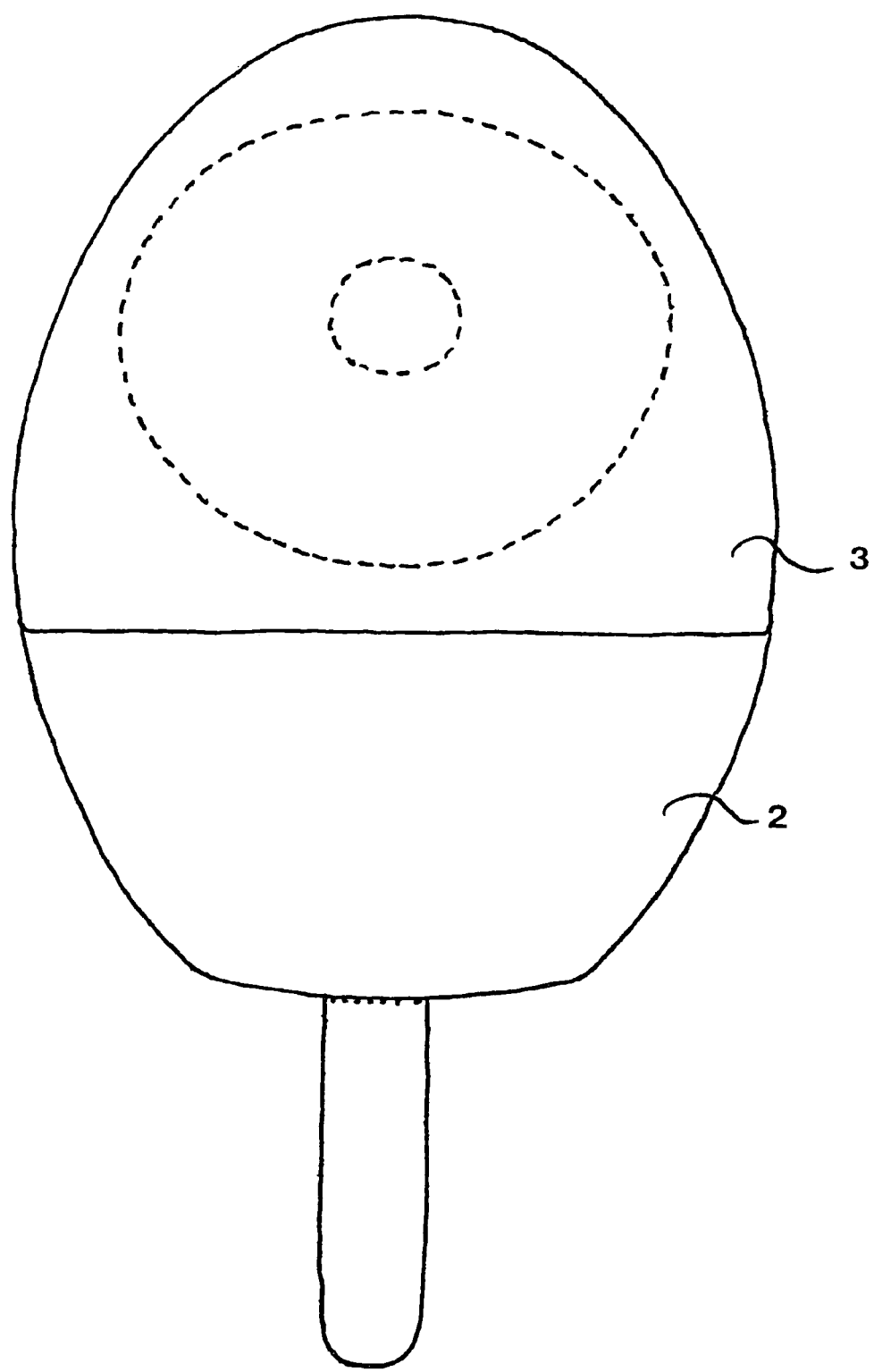
FIG. 4 shows the embodiment of FIG. 1 in an unfolded state, seen from the surface facing away from the user.

FIG. 4 shows the embodiment of FIG. 1 in an unfolded state, seen from the surface facing away from the user showing the front wall (2), the cover sheet (5) and the strip (6) extending from the bottom end and indicating an adhesive wafer situated on the back wall.

What is claimed is:

1. An ostomy receiving bag comprising:
    front and rear walls sealed along a rim of the bag, the bag having a lateral midline located between an upper end of the bag and a bottom end of the bag, the bag defining an inlet opening nearer to the upper end of the bag than to the bottom end of the bag, said inlet opening being to only opening in the bag, the bottom end of the bag for holding part of a collecting volume of the bag; and
    a cover sheet attached to the upper end of the bag at the rim and covering at least part of one of the front and the rear walls to form a pocket and provided with an unattached edge placed between the upper end of the bag and the bottom end of the bag;
    the collecting volume of the bag being reduced by at least 25% when the bottom end of the bag is placed under the cover sheet to a position between the lateral midline and the upper end of the bag.

2. The ostomy receiving bag of claim 1, wherein the front and rear walls are sealed permanently together along an entire peripheral edge of the bag.

3. The ostomy receiving bag of claim 1, wherein the cover sheet covers a portion of the front wall of the bag.

4. The ostomy receiving bag of claim 1, wherein the cover sheet covers from 25% to 100% of one of the front and the rear walls of the bag.

5. The ostomy receiving bag of claim 1, wherein the cover sheet covers from 50% to 75% of one of the front and the rear walls of the bag.

6. The ostomy receiving bag of claim 1, wherein the cover sheet is a porous material.

7. The ostomy receiving bag of claim 1, wherein the collecting volume of the bag is reduced by at least 50% when the bottom end of the bag is placed under the cover sheet to a position between the lateral midline and the upper end of the bag.

8. The ostomy receiving bag of claim 1, wherein the bottom end of the bag is permanently sealed.

9. An ostomy receiving bag comprising:
    front and rear walls sealed along a rim of the bag, the bag having a lateral midline located between an upper end of the bag and a bottom end of the bag, the bag defining an inlet opening nearer to the upper end of the bag than to the bottom end of the bag for receiving output from a stoma which is collected in the bag, said inlet opening being the only opening in said bag, the bottom end of the bag holding part of the collecting volume of the bag; and
    a cover sheet attached to the upper end of the bag at the rim and covering at least part of one of the front and the rear walls to form a pocket and provided with an unattached edge placed between the upper end of the bag and the bottom end of the bag;
    a collecting volume of the bag being reduced when the bottom end of the bag is placed under the cover sheet to a position between the lateral midline and the upper end of the bag.

10. The ostomy receiving bag of claim 9, wherein the front and rear walls are sealed permanently together along an entire peripheral edge of the bag.

11. The ostomy receiving bag of claim 9 wherein the cover sheet covers a portion of the front wall of the bag.

12. The ostomy receiving bag of claim 9, wherein the cover sheet covers from 25% to 100% of one of the front and the rear walls of the bag.

13. The ostomy receiving bag of claim 9, wherein the cover sheet covers from 50% to 75% of one of the front and the rear walls of the bag.

14. The ostomy receiving bag of claim 9, wherein the cover sheet is a porous material.

15. The ostomy receiving bag of claim 9, wherein the collecting volume of the bag is reduced by at least 25% when the bottom end of the bag is placed under the cover sheet to a position between the lateral midline and the upper end of the bag.

16. The ostomy receiving bag of claim 9, wherein the collecting volume of the bag is reduced by at least 50% when the bottom end of the bag is placed under the cover sheet to a position between the lateral midline and the upper end of the bag.

17. The ostomy receiving bag of claim 9, wherein the bottom end of the bag is permanently sealed.

18. The ostomy receiving bag of claim 9, wherein the cover is provided with an unattached edge placed between the upper end of the bag and the bottom end of the bag.

* * * * *